(12) United States Patent
Holub et al.

(10) Patent No.: US 10,479,804 B2
(45) Date of Patent: Nov. 19, 2019

(54) PREPARATION OF AMMONIUM OR PHOSPHONIUM BORATE SALTS

(71) Applicant: Gotion Inc., Fremont, CA (US)

(72) Inventors: Nicole Holub, Mannheim (DE); Juergen Herbel, Mannheim (DE)

(73) Assignee: Gotion Inc., Fremont, CA (US)

( * ) Notice: Subject to any disclaimer, the term of this patent is extended or adjusted under 35 U.S.C. 154(b) by 0 days.

(21) Appl. No.: 16/075,547

(22) PCT Filed: Jan. 27, 2017

(86) PCT No.: PCT/EP2017/051764
§ 371 (c)(1),
(2) Date: Aug. 3, 2018

(87) PCT Pub. No.: WO2017/133978
PCT Pub. Date: Aug. 10, 2017

(65) Prior Publication Data
US 2019/0040086 A1 Feb. 7, 2019

(30) Foreign Application Priority Data
Feb. 5, 2016 (EP) ..................................... 16154485

(51) Int. Cl.
*C07C 211/63* (2006.01)
*C07F 5/02* (2006.01)
*C07D 295/088* (2006.01)

(52) U.S. Cl.
CPC ............ *C07F 5/022* (2013.01); *C07C 211/63* (2013.01); *C07D 295/088* (2013.01)

(58) Field of Classification Search
CPC .............................. C07F 5/022; C97C 211/63
See application file for complete search history.

(56) References Cited

U.S. PATENT DOCUMENTS 10,065,936 B2 * 9/2018 Holub ................ C07D 295/088

FOREIGN PATENT DOCUMENTS

| WO | 9427335 A1 | 11/1994 |
| WO | 2004005222 A2 | 1/2004 |
| WO | 2013026854 A1 | 2/2013 |

* cited by examiner

*Primary Examiner* — Golam M Shameem
(74) *Attorney, Agent, or Firm* — Young Basile Hanlon & MacFarlane, P.C.

(57) ABSTRACT

A process for preparing an ammonium or phosphonium borate salt KA containing a cation K and an anion A. The process includes providing a melt of a borate salt $K^1A$, and adding a solution of an ammonium or phosphonium salt $KA^1$ in a solvent or solvent mixture (i), wherein K is an organic ammonium or phosphonium cation, and A is a borate anion of formula (Ia) or (Ib).

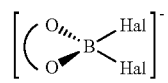

(Ia)

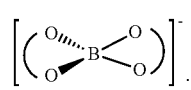

(Ib)

15 Claims, No Drawings

PREPARATION OF AMMONIUM OR PHOSPHONIUM BORATE SALTS

CROSS-REFERENCE TO RELATED APPLICATION(S)

This application is a 371 application of International Application No. PCT/EP2017/051764, filed on Jan. 27, 2017, which claims priority to European Patent Application No. 16154485.3, filed on Feb. 5, 2016, the content of which is hereby incorporated by reference in its entirety.

DETAILED DESCRIPTION

The present disclosure relates to the preparation of ammonium or phosphonium borate salts.

Non-substituted tetraalkyl ammonium borate salts are used in electrolytes in electrochemical cells, see e.g. WO 94/27335 A1. WO 94/27335 A1 describes the preparation of the tetraalkyl ammonium borates by reaction of lithium hydroxide or tetraalkylammonium hydroxide with $B(OH)_3$ and the desired bidente ligand salicylic acid or catechine. WO 94/27335 A1 also discloses the synthesis of the ammonium borates via metathesis of the lithium borate salt with a tetraalkylammonium halide.

Sulfur containing additives comprising sulfur containing ammonium or phosphonium cations and various anions including borates and their application in electrolyte compositions for electrochemical cells are described in WO 2013/026854 A1. According to WO 2013/026854 A1 the sulfur containing additives containing a borate anion like bisoxalato borate are prepared via metathesis of an ionic compound containing a sulfur containing ammonium or phosphonium cation and a halide anion with an alkali salt of the borate anion, e.g. lithium bisoxalato borate.

Up to now lithium borates are an expensive raw material. The not yet published European patent application EP 15154303.0 describes the preparation of salts of sulfur containing ammonium and phosphonium cations and various borate anions. According to EP 15154303.0 a first salt comprising a sulfur containing ammonium and phosphonium cation and an organic sulfonate or halide anion is brought into contact with a second salt composed of a tetraalkyl ammonium cation and a borate anion in the presence of a solvent. It turned out that in case salts of borate anions comprising halides like difluoro oxalato borate are prepared, yields may not be as good as good as expected in case of salts comprising a non-halide containing borate due to possible decomposition of the halide containing borate anions in the presence of protic solvents. Protic solvents on the other hand are beneficial for crystallizing and recrystallizing the desired borate salts.

It was an object of the present disclosure to provide a process for preparing ammonium and phosphonium borates which can be used as alternative to the known processes and which does not require the lithium borate salts. The process shall be cost effective, should allow the use of educts which are easy to prepare, and should allow the efficient preparation of ammonium and phosphonium borates, in particular of ammonium and phosphonium borate salts wherein the borate anion is susceptible to decomposition in protic solvents, e.g. contains halide ligands.

These objects are achieved by a process for preparing an ammonium or phosphonium borate salt KA containing a cation K and an anion A comprising the steps
providing a melt of a borate salt $K^1A$,
adding a solution of an ammonium or phosphonium salt $KA^1$ in a solvent or solvent mixture (i),
wherein
K is an organic ammonium or phosphonium cation;
A is a borate anion of formula (Ia) or (Ib)

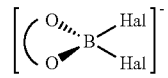  (Ia)

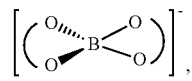  (Ib)

wherein Hal is halogen, and

is a bidentate radical derived from a 1,2-, 1,3- or 1,4-diol, from a 1,2-, 1,3- or 1,4-dicarboxylic acid or from a 1,2-, 1,3- or 1,4-hydroxycarboxylic acid by abstracting the two H atoms of pairs of adjacent OH groups of the respective diol, hydroxycarboxylic acid or dicarboxylic acid in 1,2-, 1,3- or 1,4-position;
$A^1$ is an organic or inorganic anion; and
$K^1$ is an ammonium cation different from K.

The ammonium or phosphonium borates KA are prepared by providing a melt of $K^1A$ and adding a solution of $KA^1$. The ammonium borate salt $K^1A$ is easily obtainable and less expensive than the analogue lithium borate salts. The salt $K^1A$ is provided as melt and possible decomposition reactions due to the presence of protic solvents are reduced.

In the following the disclosure is described in detail.

K is an organic ammonium or phosphonium cation. An organic ammonium or phosphonium cation comprise a central N- or P-atom, which is substituted by 4 substituents selected from H and hydrogencarbons, which may comprise one or more organic functional groups like ether groups, sulfonic acid ester groups, carboxylic ester groups, and carbonate groups and wherein the hydrocarbons may be substituted.

K may be selected from $[XR^1R^2R^3R^4]^+$
wherein X is selected from P and N;
$R^1$, $R^2$, $R^3$, and $R^4$ are selected independently from each other from optionally substituted $C_1$-$C_{20}$ alkyl, $C_2$-$C_{20}$ alkenyl, $C_2$-$C_{20}$ alkynyl, $C_5$-$C_{12}$ (hetero)aryl, and $C_6$-$C_{30}$ (hetero)aralkyl, wherein one or more $CH_2$ groups of alkyl, alkenyl, alkynyl and aralkyl which are not directly bound to the X-atom may be replaced by O, 1,2-epoxyethylene, cyclopropylene, $OSO_2$, $SO_2O$, $OC(O)$, $C(O)O$, $OC(O)O$, or $OC(O)C(O)O$;
or wherein $R^1$ and $R^2$ are linked and jointly selected from a 4- to 5-membered hydrocarbon group forming together with the central X-atom a five- or six-membered heterocycle which may be substituted by one or more substituents selected from $C_1$-$C_{10}$ alkyl, and wherein one or more members of the 4- to 5-membered hydrocarbon group may be replaced by one or more O, S or NR';
R' is selected from H, $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ (hetero)aralkyl, which may be substituted by one or more groups selected from F, cyclopropyl, 1,2-epoxyethyl, and sulfonate, and wherein one or more CH₂ groups of alkyl, alkenyl, alkynyl and (hetero)aralkyl which are not directly bound to the N-atom may be replaced by O, 1,2-epoxyethylene, cyclopropylene, OSO₂ or SO₂O.

The term "$C_1$-$C_{20}$ alkyl" as used herein means a straight or branched saturated hydrocarbon group with 1 to 20 carbon atoms having one free valence and includes, e.g., methyl, ethyl, n-propyl, iso-propyl, n-butyl, sec-butyl, iso-butyl, tert-butyl, n-pentyl, iso-pentyl, 2,2-dimethylpropyl, n-hexyl, iso-hexyl, 2-ethyl hexyl, n-heptyl, iso-heptyl, n-octyl, iso-octyl, n-nonyl, n-decyl and the like. Preferred are $C_1$-$C_{10}$ alkyl groups, more preferred are $C_1$-$C_6$ alkyl groups, even more preferred are $C_1$-$C_4$ alkyl groups, and most preferred are methyl, ethyl, and 1- and 2-propyl.

The term "$C_2$-$C_{20}$ alkenyl" as used herein refers to an unsaturated straight or branched hydrocarbon group with 2 to 20 carbon atoms having one free valence. Unsaturated means that the alkenyl group contains at least one C=C double bond. $C_2$-$C_{20}$ alkenyl includes for example ethenyl, 1-propenyl, 2-propenyl, 1-n-butenyl, 2-n-butenyl, iso-butenyl, 1-pentenyl, 1-hexenyl, 1-heptenyl, 1-octenyl, 1-nonenyl, 1-decenyl and the like. Preferred are $C_2$-$C_{10}$ alkenyl groups, more preferred are $C_2$-$C_6$ alkenyl groups, even more preferred are $C_2$-$C_4$ alkenyl groups and in particular preferred are ethenyl and 1-propen-3-yl (allyl).

The term "$C_2$-$C_{20}$ alkynyl" as used herein refers to an unsaturated straight or branched hydrocarbon group with 2 to 20 carbon atoms having one free valence, wherein the hydrocarbon group contains at least one C—C triple bond. $C_2$-$C_{20}$ alkynyl includes for example ethynyl, 1-propynyl, 2-propynyl, 1-n-butinyl, 2-n-butynyl, iso-butinyl, 1-pentynyl, 1-hexynyl, -heptynyl, 1-octynyl, 1-nonynyl, 1-decynyl and the like. Preferred are $C_2$-$C_{10}$ alkynyl, more preferred are $C_2$-$C_6$ alkynyl, even more preferred are $C_2$-$C_4$ alkynyl, in particular preferred are ethynyl and 1-propyn-3-yl (propargyl).

The term "$C_5$-$C_{12}$ (hetero)aryl" as used herein denotes an aromatic 5- to 12-membered hydrocarbon cycle or condensed cycles having one free valence wherein one or more of the C-atoms of the aromatic cycle(s) may be replaced independently from each other by a heteroatom selected from N, S, O and P. Examples of $C_6$-$C_{12}$ (hetero)aryl are phenyl, naphtyl, pyrrolyl, furanyl, thiophenyl, pyridinyl, pyranyl, and thiopyranyl. Preferred is phenyl.

The term "$C_6$-$C_{30}$ (hetero)aralkyl" as used herein denotes an aromatic or heteroaromatic 5- to 12-membered aromatic hydrocarbon cycle or condensed aromatic or heteroaromatic cycles as defined above substituted by one or more $C_1$-$C_6$ alkyl. The $C_6$-$C_{30}$ (hetero)aralkyl group contains in total 6 to 30 C-atoms and has one free valence. The free valence may be located at the aromatic cycle or at a $C_1$-$C_6$ alkyl group, i.e. $C_6$-$C_{30}$ aralkyl group may be bound via the aromatic part or via the alkyl part of the (hetero)aralkyl group. Examples of $C_6$-$C_{30}$ (hetero)aralkyl are methylphenyl, 1,2-dimethylphenyl, 1,3-dimethylphenyl, 1,4-dimethylphenyl, ethylphenyl, 2-i-propylphenyl, 2-methylfuryl, 2-methylpyridiyl, and the like.

The term "sulfonate" as used herein means the groups —S(O)₂O—$R^v$ or —OS(O)₂—$R^v$ wherein $R^v$ is selected from $C_1$-$C_{10}$ alkyl, preferably from $C_1$-$C_6$ alkyl and more preferred from $C_1$-$C_4$ alkyl.

The term "cyclopropylene" as used herein means the group derived from cyclopropane molecule having two free valences at two adjacent C-atoms:

the asterisks denote the two free valences.

The term "1,2-epoxyethyl" as used herein means an oxirane cycle having one free valence:

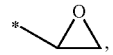

the asterisk denotes the free valence.

The term "1,2-epoxyethylene" as used herein means an oxirane cycle having two free valences at the two adjacent C-atoms:

the asterisks denote the free valences.

The term "optionally substituted $C_1$-$C_{20}$ alkyl, $C_2$-$C_{20}$ alkenyl, $C_2$-$C_{20}$ alkynyl, $C_5$-$C_{12}$ (hetero)aryl, and $C_6$-$C_{30}$ (hetero)aralkyl" means that each of the alkyl, alkenyl, alkynyl, (hetero)aryl and (hetero)aralkyl group may be substituted, e.g. by groups selected from F, cyclopropyl, 1,2-epoxyethyl, and sulfonate.

X is N or P; preferably X is N.

Preferably $R^1$, $R^2$, $R^3$, and $R^4$ are selected independently from each other from $C_1$-$C_{10}$ alkyl, $C_2$-$C_{10}$ alkenyl, $C_2$-$C_{10}$ alkynyl, $C_5$-$C_7$ (hetero)aryl, and $C_6$-$C_{18}$ (hetero)aralkyl, which may be substituted by one or more groups selected from F, cyclopropyl, 1,2-epoxyethyl, and sulfonate, and wherein one or more CH₂ groups of alkyl, alkenyl, alkynyl and (hetero)aralkyl which are not directly bound to the X-atom may be replaced by O, 1,2-epoxyethylene, cyclopropylene, OSO₂ or SO₂O;

or $R^1$ and $R^2$ are linked and jointly selected from a 4- to 5-membered hydrocarbon group forming together with the central X-atom a five- or six-membered heterocycle which may be substituted by one or more substituents selected from $C_1$-$C_{10}$ alkyl, and wherein one or more members of the 4- to 5-membered hydrocarbon group may be replaced by one or more O, S or NR'.

The five- or six-membered heterocycle formed by $R^1$ and $R^2$ and the central X-atom may be selected for example from

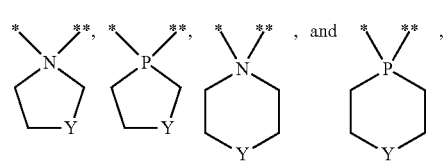

wherein Y is CH₂, O, S or NR' and the asterisks denote the bonds to $R^3$ and $R^4$, respectively. Examples of five- or six-membered heterocycles formed by $R^1$ and $R^2$ and the central X-atom are pyrrolidine, piperidine, and morpholine.

If $R^1$ and $R^2$ are not linked, $R^1$ and $R^2$ are preferably selected independently from each other from $C_1$-$C_6$ alkyl, $C_2$-$C_6$ alkenyl, $C_2$-$C_6$ alkynyl, $C_5$-$C_7$ (hetero)aryl, and $C_6$-$C_{18}$ (hetero)aralkyl, and more preferred from $C_1$-$C_4$ alkyl, $C_2$-$C_4$ alkenyl, $C_2$-$C_4$ alkynyl, $C_5$-$C_7$ (hetero)aryl, and $C_6$-$C_{14}$ (hetero)aralkyl, and most preferred from $C_1$-$C_4$ alkyl, $C_2$-$C_4$ alkenyl, and $C_2$-$C_4$ alkynyl, wherein alkyl, alkenyl, alkynyl, (hetero)aryl and (hetero)aralkyl may be substituted one or more groups selected from F, cyclopropyl, 1,2-epoxyethyl and sulfonate, and wherein one or more $CH_2$ group of alkyl, alkenyl, alkynyl and (hetero)aralkyl which are not directly bound to the X-atom may be replaced by O, 1,2-epoxyethylene, cyclopropylene, $OSO_2$ or $SO_2O$.

If $R^1$ and $R^2$ are linked they are preferably jointly selected from a 4-membered hydrocarbon group forming together with the central X-atom a five-membered heterocycle which may be substituted by one or more substituents selected from F and optionally fluorinated $C_1$-$C_{10}$ alkyl, preferably from F and optionally fluorinated $C_1$-$C_4$ alkyl, and wherein one or more members of the 4-membered hydrocarbon group may be replaced by O, S or NR'. The preferred five-membered heterocycle formed by $R^1$ and $R^2$ and the central X-atom is pyrrolidine.

$R^1$ and $R^2$ are preferably linked and jointly selected from a 4- to 5-membered hydrocarbon group forming together with the central X-atom a five- or six-membered heterocycle, which may be substituted by one or more substituents selected from F and optionally fluorinated $C_1$-$C_{10}$ alkyl, and wherein one or more members of the 4- to 5-membered hydrocarbon group may be replaced by O, S or NR', more preferred they are selected from a 4-membered hydrocarbon group forming together with the central X-atom a five-membered heterocycle, which may be substituted by one or more substituents selected from F and optionally fluorinated $C_1$-$C_{10}$ alkyl, and wherein one or more members of the 4-membered hydrocarbon group may be replaced by O, S or NR'.

$R^3$ and $R^4$ are preferably selected from optionally substituted $C_1$-$C_{10}$ alkyl, $C_2$-$C_{10}$ alkenyl, $C_2$-$C_{10}$ alkynyl, $C_5$-$C_{12}$ (hetero)aryl, and $C_6$-$C_{24}$ (hetero)aralkyl, more preferred from $C_1$-$C_6$ alkyl, $C_2$-$C_6$ alkenyl, $C_2$-$C_6$ alkynyl, $C_5$-$C_7$ (hetero)aryl, and $C_6$-$C_{18}$ (hetero)aralkyl, even more preferred from $C_1$-$C_6$ alkyl, $C_2$-$C_6$ alkenyl, and $C_2$-$C_6$ alkynyl, wherein one or more $CH_2$ groups of alkyl, alkenyl, alkynyl and (hetero)aralkyl which are not directly bound to the X-atom may be replaced by O, 1,2-epoxyethylene, cyclopropylene, $OSO_2$, $SO_2O$, OC(O), C(O)O, OC(O)O, or OC(O)C(O)O.

It is preferred if at least one of $R^3$ and $R^4$ comprises an optionally substituted alkyl, alkenyl, alkynyl and (hetero)aralkyl group wherein at least one $CH_2$ group which is not directly bound to the X-atom is replaced by $OSO_2$ or $SO_2O$.

It is preferred if $R^4$ is L-$OSO_2R^{4a}$, i.e. preferred cations A are cations of formula (II)

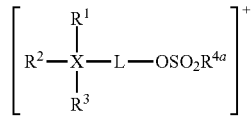
(II)

wherein $R^1$, $R^2$, and $R^3$ are selected as defined above or as preferred,

L is a —$(CH_2)_n$— chain wherein one or more $CH_2$ groups of the —$(CH_2)_n$— chain which are not directly bound to the X-atom or the $OSO_2$ group may be replaced by O and wherein a C—C single bond between two adjacent $CH_2$ groups of the —$(CH_2)_n$-chain may be replaced by a C—C double bond or a C—C triple bond;

n is an integer from 1 to 8;

$R^{4a}$ is selected from $C_1$-$C_{18}$ alkyl, $C_2$-$C_{18}$ alkenyl, $C_2$-$C_{18}$ alkynyl, $C_5$-$C_{12}$ (hetero)aryl, and $C_6$-$C_{22}$ (hetero)aralkyl, which may be substituted by one or more groups selected from F, cyclopropyl, 1,2-epoxyethyl, and sulfonate, and wherein one or more $CH_2$ groups of alkyl, alkenyl, alkynyl and (hetero)aralkyl which are not directly bound to the $OSO_2$ group may be replaced by O, 1,2-epoxyethylene, cyclopropylene, $OSO_2$ or $SO_2O$.

n is an integer selected from 1, 2, 3, 4, 5, 6, 7, and 8, preferably n is 1, 2, 3 or 4, more preferred n is 2, 3 or 4.

Preferably L is a non-substituted alkylene chain with n being selected as defined above.

$R^{4a}$ is selected from $C_1$-$C_{18}$ alkyl, $C_2$-$C_{18}$ alkenyl, $C_2$-$C_{18}$ alkynyl, $C_5$-$C_{12}$ (hetero)aryl, and $C_6$-$C_{22}$ (hetero)aralkyl, preferably $R^{4a}$ is selected from $C_1$-$C_{10}$ alkyl, $C_2$-$C_{10}$ alkenyl, $C_2$-$C_{10}$ alkynyl, $C_5$-$C_7$ (hetero)aryl, and $C_6$-$C_{18}$ (hetero)aralkyl, and more preferred $C_1$-$C_6$ alkyl, $C_2$-$C_6$ alkenyl, $C_2$-$C_6$ alkynyl, $C_5$-$C_7$ (hetero)aryl, and $C_6$-$C_{18}$ (hetero)aralkyl, which may be substituted by one or more groups selected from F, cyclopropyl, 1,2-epoxyethyl, and sulfonate, and wherein one or more $CH_2$ groups of alkyl, alkenyl, alkynyl and (hetero)aralkyl which are not directly bound to the $OSO_2$ group may be replaced by O, 1,2-epoxyethylene, cyclopropylene, $OSO_2$ or $SO_2O$; in particular preferred $R^{4a}$ is selected from methyl, ethyl, propyl, ethenyl, 1-propen-3-yl, ethynyl, and 1-propyn-3-yl.

An example for a cation K is 1-methyl-1-(2-((methylsulfonyl)oxy)ethyl)-pyrrolidinium.

A is a borate anion of formula (Ia) or (Ib) as defined above.

is independently at each occurrence a bidentate radical derived from a 1,2-, 1,3- or 1,4-diol, from a 1,2-, 1,3- or 1,4-dicarboxylic acid or from a 1,2-, 1,3- or 1,4-hydroxycarboxylic acid by abstracting the two H atoms of pairs of adjacent OH groups of the respective diol, hydroxycarboxylic acid or dicarboxylic acid in 1,2-, 1,3- or 1,4-position.

The term "adjacent OH groups" means the two hydroxyl groups present in the respective functional groups in 1,2-, 1,3- or 1,4-position, i.e. the two OH-groups present in the two carboxylic acid groups of a 1,2-, 1,3- or 1,4-dicarboxylic acid, the two OH-groups present in a 1,2-, 1,3- or 1,4-diol or the two OH-groups present in the carboxylic acid group and the alcoholic OH-group of a 1,2-, 1,3- or 1,4-hydroxycarboxylic acid.

Suited 1,2-, 1,3- and 1,4-diols from which the bidentate radical is derived may be aliphatic or aromatic and are optionally substituted by one or more F and/or by at least one straight or branched non-fluorinated, partly fluorinated or fully fluorinated $C_1$-$C_4$ alkyl group. They may be selected, e.g., from 1,2-dihydroxybenzene, ethane-1,2-diol, propane-1,2-diol, butane-1,2-diol, propane-1,3-diol, butan-1,3-diol, butan-1,4-diol, cyclohexyl-trans-1,2-diol and naphthalene-2,3-diol which are optionally are substituted by one or more F and/or by at least one straight or branched non-fluorinated, partly fluorinated or fully fluorinated $C_1$-$C_4$ alkyl group. An example for such 1,2- or 1,3-diole is 1,1,2,2-tetra(trifluoromethyl)-1,2-ethane diol.

"Fully fluorinated $C_1$-$C_4$ alkyl group" means, that all H-atoms of the alkyl group are substituted by F.

Suited 1,2-, 1,3- and 1,4-dicarboxlic acids from which the bidentate radical is derived may be aliphatic or aromatic. Examples are oxalic acid, malonic acid (propane-1,3-dicarboxylic acid), succinic acid, phthalic acid and isophthalic acid, preferred is oxalic acid. The 1,2-, 1,3- and 1,4-dicarboxlic acid are optionally substituted by one or more F and/or by at least one straight or branched non-fluorinated, partly fluorinated or fully fluorinated $C_1$-$C_4$ alkyl group.

Suited 1,2-, 1,3- and 1,4-hydroxycarboxylic acids from which the bidentate radical is derived may be aliphatic or aromatic and are optionally substituted by one or more F and/or by at least one straight or branched non-fluorinated, partly fluorinated or fully fluorinated $C_1$-$C_4$ alkyl group. Examples of 1,2-, 1,3- and 1,4-hydroxycarboxylic acids are salicylic acid, tetrahydro salicylic acid, malic acid, and 2-hydroxy acetic acid, which are optionally substituted by one or more F and/or by at least one straight or branched non-fluorinated, partly fluorinated or fully fluorinated $C_1$-$C_4$ alkyl group. An example for a fluorinated 1,2-hydroxycarboxylic acid is 2,2-bis(trifluoromethyl)-2-hydroxy-acetic acid.

Preferably

is a bidentate radical derived from 1,2- and 1,3-hydroxycarboxylic acids, 1,2- and 1,3-dicarboxlic acids, and 1,2- and 1,3-diols, more preferred

is a bidentate radical derived from 1,2-hydroxycarboxylic acids, 1,2-dicarboxlic acids, and 1,2-diols, e.g.

is oxalic acid, salicylic acid, or phthalic acid.

Hal is halogen, e.g. F, Cl, Br, or I. Preferably Hal is F.

In case of anions A of formula (Ib), the two bidentate radicals

may be same or different, preferably they are the same.

Within the anions A as defined above, anions A of formula (Ia) are preferred, in particular anions A of formula (Ia) are preferred wherein Hal is F.

Examples of borate anions of formula (Ia) and (Ib) are bis-1,2-benzenediolato borate, bissalicylato borate, difluoro oxalato borate, difluoro benzenediolato borate, difluoro salicylato borate, difluoro malonato borate, and bisoxalato borate. Anion A is preferably selected from difluoro oxalato borate and bisoxalato borate, a particular preferred anion A is difluoro oxalato borate.

$K^1$ is an ammonium cation different from K. Examples of ammonium cation $K^1$ are cations of formula $[NR^5R^6R^7R^8]^+$ wherein $R^5$, $R^6$, $R^7$, and $R^8$ are selected independently from each other from H and $C_1$-$C_{20}$ alkyl, preferred from H and $C_1$-$C_{10}$ alkyl and more preferred from H and $C_1$-$C_6$ alkyl, or wherein $R^5$ and $R^6$ are linked and jointly selected from a 4- to 5-membered hydrocarbon group forming together with the central N-atom a five- or six-membered heterocycle which may substituted by one or more substituents selected from $C_1$-$C_{10}$ alkyl, and wherein one or more member of the 4- to 5-membered hydrocarbon group may be replaced by one or more O, S or NR", R" is selected from H and $C_1$-$C_{10}$ alkyl.

In case $R^5$ and $R^6$ are linked they are preferably selected from a 4-membered hydrocarbon group and form together with the central N-atom a five-membered heterocycle.

Preferably at least one of $R^5$, $R^6$, $R^7$, and $R^8$ is H, more preferred at least one of $R^5$, $R^6$, $R^7$, and $R^8$ is H and simultaneously at least one of $R^5$, $R^6$, $R^7$, and $R^8$ is not H.

In particular preferred are cations $K^1$ wherein $R^5$, $R^6$, $R^7$, and $R^8$ are selected from H and $C_1$-$C_{10}$ alkyl, preferably from H and $C_1$-$C_6$ alkyl, and wherein at least one of $R^5$, $R^6$, $R^7$, and $R^8$ is not H and at least one of $R^5$, $R^6$, $R^7$, and $R^8$ is H.

Examples of cations $K^1$ are triethylammonium $[(C_2H_5)_3NH]^+$, dimethylethylammonium $[(C_2H_5)(CH_3)_2NH]^+$, diisopropylethylammonium $[(C_2H_5)(iC_3H_7)_2NH]^+$, N-methylpyrrolidinium, and isopropylammonium $[iC_3H_7NH_3]+$. In particular preferred are triethylammonium and isopropylammonium.

A very preferred salt $K^1A$ is isopropylammonium difluoro oxalato borate. Isopropylammonium difluoro oxalato borate has a comparatively low melting point of about 40° C. Using it as $K^1A$ allows a comparative low temperature in step (a) of the preparation process. Lower temperature leads to less decomposition of the difluoro oxalato borate and to higher yields of the desired product KA.

The anion $A^1$ is an organic or inorganic anion and may be selected from organic sulfonates, Cl⁻, Br⁻, and I⁻. The organic sulfonates may be selected from sulfonates of formula $[R^9—SO_3]^-$ wherein $R^9$ is selected from $C_1$-$C_{20}$ alkyl, $C_2$-$C_{20}$ alkenyl, $C_2$-$C_{20}$ alkynyl, $C_5$-$C_{12}$ (hetero)aryl, and $C_6$-$C_{24}$ (hetero)aralkyl, and preferred from $C_1$-$C_6$ alkyl, $C_2$-$C_6$ alkenyl, $C_2$-$C_6$ alkynyl, $C_5$-$C_7$ (hetero) aryl, and $C_6$-$C_{18}$ (hetero)aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the $OSO_2$ group may be replaced by O, 1,2-epoxyethylene, cyclopropylene, $OSO_2$ or $SO_2O$; in particular preferred $R^9$ is selected from methyl, ethyl, propyl, ethenyl, and 1-propyn-3-yl. An example of an organic sulfonate which can be used as $A^1$ is $[CH_3—SO_3]^-$. In case $A^1$ is $[R^9—SO_3]^-$ no halide anions are used which have to be removed carefully if compound KA is used in lithium ion batteries, since halides may have a detrimental effect on the life time of lithium ion batteries.

Anion $A^1$ is usually different from anion A.

Especially preferred $A^1$ is an anion selected from $[R^9—SO_3]^-$ and K is an anion of formula (II) wherein $R^{4a}$ and $R^9$ are same. Such compounds wherein $R^{4a}$ and $R^9$ are same are easily prepared in one step as described below. The use of symmetrical educts for the preparation of $KA^1$ which are substituted twice by the same substituent $SOR^{4a}$ in comparison to educts which are unsymmetrically substituted is simpler. The synthesis of $KA^1$ from educts substituted by halogen and $SOR^{4a}$ is more complicated and expensive.

In a preferred embodiment of the preparation process

K is a cation of formula (II), wherein X is N, $R^1$ and $R^2$ form together with the central X-atom a five-membered heterocycle, $R^3$ and $R^{4a}$ are selected from $C_1$ to $C_6$ alkyl, and L is a —$(CH_2)_n$— chain with n=1, 2, 3 or 4;

A is an anion selected from bis(oxalato) borate and difluoro oxalato borate;

$K^1$ is a cation selected from $[NR^5R^6R^7R^8]^+$ wherein $R^5$, $R^6$, $R^7$, and $R^8$ are selected independently from each other from H and $C_1$-$C_6$ alkyl or wherein $R^5$ and $R^6$ are linked and jointly selected from —$(CH_2)_4$— alkylene forming together with the central N-atom a five-membered heterocycle and $R^8$ is selected independently from $R^5$, $R^6$, and $R^7$ from H and $C_1$-$C_6$ alkyl, preferably $R^8$ is H; and $A^1$ is an anion selected from $[R^9—SO_3]^-$ wherein $R^9$ is selected from $C_1$-$C_6$ alkyl.

In step (a) a melt of a borate salt $K^1A$ is provided. The melt of the borate salt $K^1A$ may be provided in any suited vessel, e.g. a bulb, beaker, reactor, container, tube, etc. It is advantageous to provide the melt of the borate salt in a temperature-controlled vessel, it is particular advantageous to use a vessel which can be cooled.

To keep the temperature low during the preparation process and to enable rapid cooling of the mixture it is beneficial to use borate salts $K^1A$ which have a low melting point, e.g. below 100° C., preferred below 70° C., more preferred below 55° C. and in particular preferred the melting point of $K^1A$ is ≤48° C.

In step (b) a solution of an ammonium or phosphonium salt $KA^1$ in a solvent or solvent mixture (i) is added to the melt of the borate salt $K^1A$ provided in step (a).

Any solvent or solvent mixture suitable may be used, e.g. the solvent or solvent mixture (i) may be selected from water, $C_1$ to $C_6$ alcohols, di-$C_1$ to $C_6$ alkylethers, $C_1$ to $C_4$ carboxylic acids, $C_1$ to $C_4$ alkylesters, di-$C_1$ to $C_4$ alkyl carbonates, acetonitrile and $C_1$ to $C_4$ ketones and mixtures thereof.

The term "$C_1$ to $C_6$ alcohol" means an alcohol containing 1 to 6 C-atoms and at least one alcoholic OH-group. Examples of $C_1$ to $C_6$ alcohols include methanol, ethanol, n-propanol, i-propanol and the like, preferred is methanol.

Examples of di-$C_1$-$C_6$-alkylethers are dimethylether, ethylmethylether, diethylether, diisopropylether, di-n-butylether, and methyl-tert-butylether, preferred is methyl-tert-butylether.

The term "$C_1$ to $C_4$ carboxylic acid $C_1$ to $C_4$ alkylester" means an ester of a carboxylic acid containing 1 to 4 C-atoms and an alcohol containing 1 to 4 C-atoms. Examples of $C_1$ to $C_4$ carboxylic acid $C_1$ to $C_4$ alkylester are methyl formiate, ethyl formiate, methyl acetate, ethyl acetate, methyl proprionate and methyl butanoate. Preferred are methyl acetate and ethyl acetate.

Di-$C_1$ to $C_4$ alkyl carbonates are acyclic organic carbonates, wherein each $C_1$ to $C_4$ alkyl group is selected independently from each other. Examples are diethyl carbonate (DEC), ethyl methyl carbonate (EMC), dimethyl carbonate (DMC), and methylpropyl carbonate. Preferred are diethyl carbonate (DEC), ethyl methyl carbonate (EMC), and dimethyl carbonate (DMC).

Examples of $C_1$ to $C_4$ ketones are acetone and ethylmethylketone. Preferred is acetone.

Preferably the solvent or solvent mixture (i) contains at least one protic solvent. Protic solvents are known to the person skilled in the art as solvents containing at least one functional group that can release a proton, e.g. solvents containing at least one H-atom bound to an oxygen as in a hydroxyl group or nitrogen atom as in an amine group. Examples for protic solvents are water, alcohols, carboxylic acids, amines and amides. Preferably the solvent or solvent mixture (i) contains at least 5 wt.-% of one or more protic solvents, more preferred at least 10 wt %. More preferred the solvent or solvent mixture (i) contains at least one solvent selected from water and $C_1$ to $C_6$ alcohols, even more preferred the solvent or solvent mixture (i) contains at least 5 wt.-% of one or more solvents selected from water and $C_1$ to $C_6$ alcohols, in particular preferred the solvent or solvent mixture (i) is selected from water and $C_1$ to $C_6$ alcohols and mixtures thereof.

$KA^1$ is present in the solvent or solvent mixture (i) in dissolved form. A solution of a compound means herein that the compound is soluble in the solvent or solvent mixture at a concentration of at least 1 g/L at 25° C.

The molar ratio of $K^1A$ to $KA^1$ used in step (b) is preferably above 1:1. The upper limit of the molar ratio of $K^1A$ to $KA^1$ used in step (b) is preferably 2:1.

After addition of the solution of $KA^1$ in step (b) the melt of $K^1A$ and the solution is usually mixed, e.g. by stirring and/or shaking.

During or after step (b) compounds KA and $K^1A^1$ are separated from each other. One possibility is to precipitate one of the two compounds KA or $K^1A^1$ while the other compound is maintained as solution in the solvent or solvent mixture (i). Afterwards the compound in precipitate form is separated from the solution of the other compound in the solvent or solvent mixture (i). Preferably compound KA is precipitated during or after step (b) and is separated from the mixture containing the solvent or solvent mixture (i) and $K^1A^1$ in dissolved form.

Precipitation of one of the two compounds KA or $K^1A^1$ may be induced for example by choosing the solvent or solvent mixture (i) such that one of the compounds KA or $K^1A^1$ is not or only partially soluble in the solvent or solvent mixture (i), preferably the solubility of either KA or $K^1A^1$ in the solvent or solvent mixture (i) in step (b) is at maximum 10 mg/L at 25° C. It is also possible to amend the solubility of KA or $K^1A1$, respectively, by adding a non-solvent for one of KA or $K^1A^1$ to the mixture obtained in step (b) or by changing the composition of the solvent mixture by removing solvent by distillation. Another possibility is to decrease the solubility of one of KA or $K^1A^1$ in the mixture obtained in step (b) by lowering the temperature of the mixture obtained in step (b), i.e. the mixture obtained in step (b) is cooled.

Precipitation of one of the two compounds KA or $K^1A^1$ may also be induced or accelerated by scratching the wall of a glass vessel containing the reaction mixture with a glass rod or using a reaction vessel comprising built-in components with extra-surfaces for inducing crystallization or by adding seed crystals like small particles of the compound KA or $K^1A^1$ to crystallize or fine solid particles like sand, silica gel particles etc.

Preferably compound KA is precipitated during or after step (b), more preferred compound KA is precipitated during step (b) by choosing the solvent or solvent mixture (i) such that KA is not or only partially soluble in the solvent or solvent mixture (i) and/or compound KA is precipitated after step (b) by decreasing the solubility of KA in the mixture obtained in step (b) by decreasing the temperature of the mixture obtained in step (b). According to one embodiment the temperature of the mixture obtained in step (b) is decreased.

For illustration purposes the different possible ways of precipitating selectively KA or $K^1A^1$ during after step (b) by adjusting the solvents is described in the following in respect of precipitating selectively KA. One alternative comprises using a solvent or solvent mixture (i) which is a solvent for $KA^1$ and $K^1A^1$ and but a non-solvent for KA, i.e. KA is not or only partially soluble in the resulting mixture. It is also possible to alter the solvent(s) present in the mixture obtained in step (b) into a non-solvent for KA by adding a non-solvent or by decreasing the temperature of the mixture obtained in step (b) whereas $K^1A^1$ stays in the dissolved form.

It is preferred to keep the temperature during step (b) and the separation of KA and $K^1A^1$ low. One possibility of keeping the temperature low is to apply cooling during step (b). Another possibility is to keep the temperature of the solution of salt $KA^1$ added below the temperature of the melt of $K^1A$, i.e. the temperature of the solution of the ammonium or phosphonium salt $KA^1$ added in step (b) is lower than the temperature of the melt of the borate salt $K^1A$ provided in step (a). Preferably the temperature of the solution of the ammonium or phosphonium salt $KA^1$ added in step (b) is below 25° C.

If the borate anion A is a borate anion of formula (Ia) wherein Hal is F, e.g. difluoro oxalato borate, it is preferred to provide a salt $K^1A$ in step (a) which was prepared by reacting one or more $BF_3$ sources (A); a dihydric compound selected from 1,2-, 1,3- and 1,4-diols, 1,2-, 1,3- and 1,4-dicarboxylic acids, and 1,2-, 1,3- and 1,4-hydroxycarboxylic acids (B); one or more second boron sources which do not contain F (C); and one or more proton acceptors (D).

As component (A) one or more $BF_3$ sources are used. Every compound which is capable to provide $BF_3$ for the reaction may be used. $BF_3$ itself is a strong Lewis acid which forms easily adducts with a large number of electron donors including ethers, alcohols, ketones, amines, phosphines, arsines, thiols, and selenides. Such adducts are capable to provide $BF_3$ for the reaction. The $BF_3$ source (A) may for example be selected from $BF_3$, $BF_3$ hydrate, $BF_3$ etherates, $BF_3$-alcohol adducts, $BF_3$-acetonitril adduct, $BF_3$-acetic acid adduct, and $BF_3$-amine adducts. Preferably the one or more $BF_3$ source (A) is selected from $BF_3$ hydrate, $BF_3$-alcohol adducts, and $BF_3$ etherates, more preferred the $BF_3$ source (A) is selected from $BF_3$ hydrate and $BF_3$-alcohol adducts, in particular preferred the $BF_3$ source (A) is selected from $BF_3$ hydrate and $BF_3$-methanol adducts.

As component (B) a dihydric compound selected from 1,2-, 1,3- and 1,4-diols, 1,2-, 1,3- and 1,4-dicarboxylic acids, and 1,2-, 1,3- and 1,4-hydroxycarboxylic acids as described above is used.

As component (C) one or more second boron sources which do not contain F are used in the preparation process. During the reaction the $BF_3$ source is converted into the difluoro chelato borate anion and superfluous fluorine is released. The second boron source, which does not contain F, uptakes the superfluous fluorine released from the $BF_3$ source during the reaction and thereby is converted into a difluoro chelato borate anion of formula (Ia), too. This leads to an efficient use and high conversion of the fluorine containing educt. The second boron source may for example be selected from boric acid $B(OH)_3$ and ammonium and alkali metal salts of borate complexes of the dihydric compound used as component (B). Such borate complexes are bis(chelato) borates of formula (Ib)

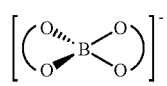
(Ib)

wherein the bidentate radical

is defined as described above or described as preferred. The alkali metal salts may be selected from the lithium, sodium, potassium or caesium salts. Usually the ammonium salts contain a cation $[NR''_4]^+$ wherein R" is selected independently from each other from H, optionally substituted $C_1$-$C_{20}$ alkyl, $C_2$-$C_{20}$ alkenyl, $C_2$-$C_{20}$ alkynyl, $C_5$-$C_{12}$ (hetero)aryl, and $C_6$-$C_{30}$ (hetero)aralkyl, wherein one or more $CH_2$ groups of alkyl, alkenyl, alkynyl and (hetero)aralkyl which are not directly bound to the X-atom may be replaced by O, 1,2-epoxyethylene, cyclopropylene, $OSO_2$, $SO_2O$, OC(O), C(O)O, OC(O)O, or OC(O)C(O)O;

or wherein two R" are linked and jointly selected from a 4- to 5-membered hydrocarbon group forming together with the central X-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or NR";

R is selected from H, $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the N-atom may be replaced by O, 1,2-epoxyethylene, cyclopropylene, $OSO_2$ or $SO_2O$.

Preferred are ammonium cations $[NR''_4]^+$ wherein R" is selected independently from each other from H, optionally substituted $C_1$-$C_{20}$ alkyl, $C_5$-$C_{12}$ (hetero)aryl, and $C_6$-$C_{30}$ (hetero)aralkyl, wherein one or more $CH_2$ groups of alkyl and (hetero)aralkyl which are not directly bound to the X-atom may be replaced by O, 1,2-epoxyethylene, cyclopropylene, $OSO_2$, $SO_2O$, OC(O), C(O)O, OC(O)O, or OC(O)C(O)O;

or wherein two R" are linked and jointly selected from a 4- to 5-membered hydrocarbon group forming together with the central X-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or NR'";

R is selected from H and $C_1$-$C_{10}$ alkyl.

More preferred are ammonium cations $[NR''_4]^+$ wherein R" is selected independently from each other from H, optionally substituted $C_1$-$C_{10}$ alkyl, $C_5$-$C_{12}$ (hetero)aryl, and $C_6$-$C_{18}$ (hetero)aralkyl;

or wherein two R" are linked and jointly selected from a 4- to 5-membered hydrocarbon group forming together with the central X-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or NR";

R'" is selected from H and $C_1$-$C_{10}$ alkyl.

In particular preferred are ammonium cations $[NR''_4]^+$ wherein R" is selected independently from each other from H, and $C_1$ to $C_6$ alkyl; or wherein two R" are linked and jointly selected from a 4- to 5-membered hydrocarbon group forming together with the central X-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or NR'''; and R''' is selected from H and $C_1$-$C_{10}$ alkyl;

Examples of such alkali metal and ammonium salts of borate complexes of the dihydric compound used as component (B) are lithium bis(oxalato) borate and triethylammonium bis(oxalato)borate. It is possible to use one, two or more different compounds as second boron source (C), e.g. boric acid and a lithium salt of the respective bis(chelatoborate). Preferably the one or more second boron source (C) is selected from boric acid and lithium and ammonium bis(chelato) borates. In particular preferred is boric acid.

In case the dihydric compound (B) is oxalic acid, the second boron source (C) which does not contain F is preferably selected from boric acid, lithium bisoxalato borate, triethylammonium bis(oxalato)borate, and mixtures thereof, more preferred the second boron source (C) is boric acid.

Usually the $BF_3$ source (A) and the second boron source (C) are used in a molar ratio ranging from 1.5:1 to 2.5:1 referred to boron. It is preferred to keep the molar ratio of $BF_3$ source (A) and second boron source (C) around 2:1, which is the optimal stoichiometric ratio. The molar ratio may for example range from 1.5:1 to 2.5:1, preferably from 1.8:1 to 2.2:1 and most preferred from 1.9:1 to 2.1:1, referred to boron, respectively. It is in particular preferred that no excess of the $BF_3$ source (A) in respect to the second boron source (C) is used, i.e. that the molar ratio of $BF_3$ source (A) and second boron source (C) is at maximum 2:1.

Additionally one or more proton acceptors (D) are used. During the formation of the difluoro chelato borate the dihydric compound (B) releases two protons per molecule. The proton acceptor (D) takes up at least part of these protons. Depending on the compounds selected as component (C) more or less of proton acceptor (D) is required. E.g., boric acid used as component (C) releases one hydroxide group per molecule. This hydroxide group can uptake one of the two protons released by the dihydric compound (D) and only the remaining one of the two protons has to be taken up by the one or more proton acceptor (D) per molecule of dihydric compound. In case a second boron source (C) like lithium bis(oxalato) borate is used, which does not release any protons during the reaction, the one or more proton acceptors (D) will uptake both protons released by the dihydric compound (B). The one or more proton acceptors (D) used in the reaction is usually selected to be different from the compounds used as components (A), (B) and (C).

The proton acceptor (D) may for example be selected from ammonia, organic amines, $NH_4OH$, organic ammonium hydroxides, and nitrogen containing aromatic heterocycles. It is possible to use one, two or more compounds as proton acceptor (D).

Examples of organic amines and organic ammonium hydroxides are organic amines $NR^{10}R^{11}R^{12}$ and organic ammonium hydroxides $[NR^{10}R^{11}R^{12}R^{13}]OH$ wherein $R^{10}$, $R^{11}$, $R^{12}$, and $R^{13}$ are selected independently from each other from H, optionally substituted $C_1$-$C_{20}$ alkyl, $C_2$-$C_{20}$ alkenyl, $C_2$-$C_{20}$ alkynyl, $C_6$-$C_{12}$ (hetero)aryl, and $C_7$-$C_{30}$ aralkyl, wherein one or more $CH_2$ groups of alkyl, alkenyl, alkynyl and aralkyl which are not directly bound to the X-atom may be replaced by O, 1,2-epoxyethylene, cyclopropylene, $OSO_2$, $SO_2O$, OC(O), C(O)O, OC(O)O, or OC(O)C(O)O;

or wherein $R^{10}$ and $R^{11}$ are linked and jointly selected from a 4- to 5-membered hydrocarbon group forming together with the central X-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or NR'';

$R^{iv}$ is selected from H, $C_1$-$C_{10}$ alkyl, $C_2$-$C_{10}$ alkenyl, $C_2$-$C_{10}$ alkynyl, $C_6$-$C_{12}$ aryl, and $C_7$-$C_{24}$ aralkyl, which may be substituted by one or more groups selected from F, cyclopropyl, 1,2-epoxyethyl, and sulfonate, and wherein one or more $CH_2$ groups of alkyl, alkenyl, alkynyl and aralkyl which are not directly bound to the N-atom may be replaced by O, 1,2-epoxyethylene, cyclopropylene, $OSO_2$ or $SO_2O$; and wherein at least one of $R^{10}$, $R^{11}$, and $R^{12}$ is not H.

Preferred organic amines and organic ammonium hydroxides for use as proton acceptor (d) are organic amines $NR^{10}R^{11}R^{12}$ and organic ammonium hydroxides $[NR^{10}R^{11}R^{12}R^{13}]OH$ wherein $R^{10}$, $R^{11}$, $R^{12}$, and $R^{13}$ are selected independently from each other from H and $C_1$-$C_{20}$ alkyl or wherein $R^{10}$ and $R^{11}$ are linked and jointly selected from a 4- to 5-membered hydrocarbon group forming together with the central N-atom a five- or six-membered heterocycle which may substituted by one or more substituents selected from $C_1$-$C_{10}$ alkyl, and wherein one or more members of the 4- to 5-membered hydrocarbon group may be replaced by one or more O, S or $NR^{iv}$; $R^{iv}$ is selected from H and $C_1$-$C_{10}$ alkyl; and wherein at least one of $R^{10}$, $R^{11}$, and $R^{12}$ is not H.

More preferred organic amines and organic ammonium hydroxides are organic amines $NR^{10}R^{11}R^{12}$ and organic ammonium hydroxides $[NR^{10}R^{11}R^{12}R^{13}]OH$ wherein $R^{10}$, $R^{11}$, $R^{12}$, and $R^{13}$ are selected independently from each other from H and $C_1$-$C_{10}$ alkyl or wherein $R^{10}$ and $R^{11}$ are linked and jointly selected from a 4- to 5-membered hydrocarbon group forming together with the central N-atom a five- or six-membered heterocycle which may substituted by one or more substituents selected from $C_1$-$C_{10}$ alkyl; and wherein at least one of $R^{10}$, $R^{11}$, and $R^{12}$ is not H.

In particular preferred organic amines and organic ammonium hydroxides are organic amines $NR^{10}R^{11}R^{12}$ and organic ammonium hydroxides $[NR^{10}R^{11}R^{12}R^{13}]OH$ wherein $R^{10}$, $R^{11}$, $R^{12}$, and $R^{13}$ are selected independently from each other from H and $C_1$-$C_6$ alkyl and wherein at least one of $R^{10}$, $R^{11}$, and $R^{12}$ is not H.

Examples of organic amines and organic ammonium hydroxides are methyl amine, ethyl amine, isopropyl amine, dimethyl amine, diethyl amine, diisopropyl amine, trimethyl amine, triethyl amine, triisopropyl amine, ethyl dimethyl amine, diethylmethyl amine, isopropyl dimethyl amine, diisopropyl methyl amine, diethyl isopropyl amine, ethyl diisopropyl amine, tetramethyl ammonium hydroxide, tetraethyl ammonium hydroxide, isopropyl ammonium hydroxide, and N-methylpyrrolidine In particular preferred are isopropyl amine and triethyl amine.

It is also possible to use nitrogen containing aromatic heterocycles as proton acceptor (D). Nitrogen containing aromatic heterocycles may for examples be selected from pyridine, pyrimidine, pyrrol, pyrazol, and imidazole.

Preferably, the proton acceptor (D) is selected from $NH_4OH$ and the organic amines and organic ammonium hydroxides as described above and as described as preferred, more preferred from the organic amines as described above and as described as preferred.

Preferably the one or more $BF_3$ sources (A) is selected from $BF_3$, $BF_3$ hydrate and B $BF_3$ alcohol adducts, the dihydric compound (B) is selected from oxalic acid, salicylic acid and phthalic acid, the one or more second boron sources which do not contain F (C) is selected from boric acid and lithium and ammonium salts of the dihydric compound (B) wherein the ammonium salt comprise a cation $[NR''_4]^+$ wherein R'' is selected independently from each other from H, and $C_1$ to $C_6$ alkyl; or wherein two R are linked and jointly selected from a 4- to 5-membered hydrocarbon group forming together with the central X-atom a five- or six-membered heterocycle which may substituted by one or more substituents selected from $C_1$-$C_{10}$ alkyl; and the one or more proton acceptors (D) is selected from ammonium, organic amines $NR^{10}R^{11}R^{12}$ and organic ammonium hydroxides $[NR^{10}R^{11}R^{12}R^{13}]OH$ wherein $R^{10}$, $R^{11}$, $R^{12}$, and $R^{13}$ are selected independently from each other from H and $C_1$-$C_6$ alkyl and wherein at least one of $R^{10}$, $R^{11}$, and $R^{12}$ is not H.

Preferably the proton acceptor (D) is the source for the cation $K^1$, i.e. $K^1$ is selected from $[NR^{10}R^{11}R^{12}H]^+$ or $[NR^{10}R^{11}R^{12}R^{13}]^+$.

Depending on the compounds (A) to (D) used it may be advantageous that an organic solvent or solvent mixture (E) is present in the reaction mixture of step (i), e.g. in case one or more compounds (A) to (D) are solid at the reaction temperature. Any solvent or solvent mixture suitable may be used, e.g. the solvent or solvent mixture (E) may be selected from water, $C_1$ to $C_6$ alcohols like methanol, ethanol, i-propanol and n-propanol, di-$C_1$ to $C_6$ alkylethers, $C_1$ to $C_4$ carboxylic acids, $C_1$ to $C_4$ alkylesters, di-$C_1$ to $C_4$ alkyl carbonates, acetonitrile, aromatic hydrocarbons like benzene, toluene, xylene, isopropyl benzene, and ethyl benzene, aliphatic hydrocarbons like n-hexane, n-heptane, and cyclohexane, and $C_1$ to $C_4$ ketones like acetone and mixtures thereof.

According to one embodiment of the present process wherein A is a borate anion of formula (Ia) wherein Hal is F like difluoro oxalato borate the preparation of KA comprises the steps (a1) preparing a borate salt $K^1A$ by reacting one or more $BF_3$ sources (A); a dihydric compound selected from 1,2-, 1,3- and 1,4-diols, 1,2-, 1,3- and 1,4-dicarboxylic acids, and 1,2-, 1,3- and 1,4-hydroxycarboxylic acids (B); one or more second boron sources which do not contain F (C); and one or more proton acceptors (D) as described above;

(a2) providing a melt of the borate salt $K^1A$ prepared in step (a1); and (b) adding a solution of an ammonium or phosphonium salt $KA^1$ in a solvent or solvent mixture (i).

If the borate anion A is bis(oxalato) borate it is preferred to provide a salt $K^1A$ in step (a) which was prepared by reaction of oxalic acid, $B(OH)_3$ and $NR^5R^6R^7$. In this case compound $K^1A$ is selected from $[HNR^5R^6R^7]^+$ bis(oxalato) borate. The reaction of oxalic acid, $B(OH)_3$ and $NR^5R^6R^7$ may be carried out in a solvent or solvent mixture and the solvents used and the water generated is removed by distillation during the reacting to shift the reaction equilibrium from oxalic acid and $B(OH)_3$ to bis(oxalato) borate. The reaction may be carried out in analogy to the preparation of HBOB described in WO 02/068433 A1.

According to one embodiment of the present process wherein A is bis(oxalato) borate the preparation of KA comprises the steps (a1) preparing a borate salt $K^1A$ by reacting oxalic acid, $B(OH)_3$ and $NR^5R^6R^7$;

(a2) providing a melt of the borate salt $K^1A$ prepared in step (a1); and (b) adding a solution of an ammonium or phosphonium salt $KA^1$ in a solvent or solvent mixture (i).

If an ammonium or phosphonium salt $KA^1$ is used in step (b) wherein K is a cation of formula (II) it is preferred to use an ammonium or phosphonium salt $KA^1$ which was prepared by reaction of $R^{4a}SO_2$—O-L-O—$SO_2R^9$ with $NR^1R^2R^3$. In case $R^{4a}$ and $R^9$ are same it is preferred to use $R^{4a}SO_2$—O-L-O—$SO_2R^9$ for the preparation of $KA^1$ which was prepared by reaction of HO-L-OH with $R^{4a}SO_2C_1$.

According to another embodiment of the present process wherein an ammonium or phosphonium cation K is a cation of formula (II), the preparation of KA comprises the steps (a1) preparing a compound $KA^1$ by reacting $R^{4a}SO_2$—O-L-O—$SO_2R^9$ with $NR^1R^2R^3$;

(a2) providing a melt of the borate salt $K^1A$; and (b) adding a solution of the ammonium or phosphonium salt $KA^1$ prepared in step (a1) in a solvent or solvent mixture (i).

According to a further embodiment of the present process wherein A is bis(oxalato) borate and the ammonium or phosphonium K is a cation of formula (II) the preparation of KA comprises the steps (a1) preparing a compound $KA^1$ by reacting $R^{4a}SO_2$—O-L-O—$SO_2R^9$ with $NR^1R^2R^3$;

(a2) preparing a compound $K^1A$ by reacting oxalic acid, $B(OH)_3$ and $NR^5R^6R^7$;

(a3) providing a melt of the borate salt $K^1A$ obtained in step (a2); and (b) adding a solution of the ammonium or phosphonium salt $KA^1$ prepared in step (a1) in a solvent or solvent mixture (i).

The disclosure is illustrated by the examples which follow, which do not, however, restrict the invention.

I Preparation of Triethylammonium Difluoro(Oxalatoborate)

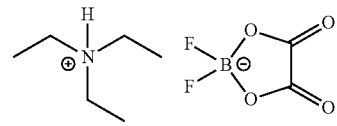

Example 1

38 g oxalic acid dihydrate, 6 g boric acid and 30 g triethylamine were mixed with 150 mL acetonitrile. 21 g Bortrifluorid-dihydrate was added and the reaction mixture was heated to 120-130° C., while volatile components were removed by distillation. The residue was further dried for 2 h at 120° C. and 10 mbar. Upon cooling, triethylammonium difluoro(oxalatoborate) was obtained as colorless, solidified melt. Quantitative F-NMR showed a purity of 92%, together with the corresponding tetrafluoro borate salt (2%) and bis(oxalatoborate) salt in 6%.

II Preparation of Isopropylammonium Difluoro(Oxalatoborate)

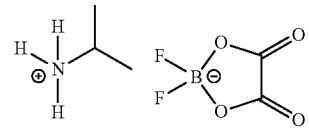

Example 2

38 g oxalic acid dihydrate, 6 g boric acid and 18 g isopropylamine were mixed with 150 mL methanol. 21 g bortrifluorid-dihydrate was added and the reaction mixture was heated to 120-130° C., while volatile components were removed by distillation. The residue was further dried for 2 h at 120° C. and 10 mbar. Upon cooling, isopropylammonium difluoro(oxalatoborate) was obtained as colorless, solidified melt in 89% yield. Quantitative F-NMR showed a purity of 90%, together with the corresponding tetrafluoro borate salt (2%) and bis(oxalatoborate) salt in 8%.

$^1$H NMR (MeOD, 400 MHz) δ (ppm)=1.39 (d, 6H), 3.38-3.52 (m, 1H). $^{19}$F NMR (MeOD, 376 MHz) δ=−154 ppm. $^{11}$B NMR (MeOD, 128 MHz) δ=3.0 ppm. Melting Point: 38° C.

III Preparation of 1-methyl-1-(2-((methylsulfonyl)oxy)ethyl)-pyrrolidinium methansulfonate

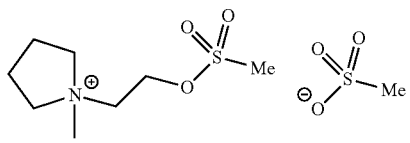

Example 3

A mixture of 40 g ethylene glycol, 163 g triethylamine, 350 g ethyl acetate and 60.5 g methyl acetate was prepared and cooled to 0° C. 170 g methanesulfonyl chloride was added in a controlled manner to ensure, that the temperature of the mixture did not exceed 25° C. The obtained suspension was stirred for additional 60 min. 325 g deionized water was added and the phases were separated. The solvents were removed at 65° C. in vacuum and the obtained raw product was used in the next step.

Isolated Yield: 85%; Purity (GC Analysis): 94 wt %

131 g 1,2-ethane diol bismethanesulfonate, obtained in the reaction above, and 360 mL methanol were stirred for 10 min, resulting in a clear solution. The solution was heated to 65° C. and 51 g N-methylpyrrolidine was added. The reaction mixture was stirred for 16 h at 65° C. Solvent and volatile compounds were removed by distillation under vacuum at 60° C. The obtained 1-methyl-1-(2-((methylsulfonyl)oxy)ethyl)-pyrrolidinium methansulfonate was directly used in the next step.

IV Preparation of 1-methyl-1-(2-((methylsulfonyl)oxy)ethyl)-pyrrolidinium difluoro(oxalatoborate)

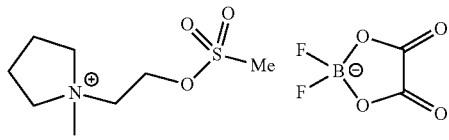

A Preparation Via Triethylammonium Difluoro(Oxalatoborate)

Example 4 (Inventive)

282 g triethylammonium difluoro(oxalatoborate) (melting point 48° C.), prepared in analogy to Example 1 was charged to a reactor and melted at 65° C. A solution of 358 g 1-methyl-1-(2-((methylsulfonyl)oxy)ethyl)-pyrrolidinium methansulfonate in methanol was added at once and the reaction mixture was cooled to 0° C. under stirring. The molar ratio of $K^1A$ to $KA^1$ was 1 At a temperature of 20° C. seed crystals of 1-methyl-1-(2-((methylsulfonyl)oxy)ethyl)-pyrrolidinium difluoro(oxalatoborate) were added, followed by stirring for additional 12 h. The suspension was filtered and the residue sequentially washed with portions of cold methanol. 1-methyl-1-(2-((methylsulfonyl)oxy)ethyl)-pyrrolidinium difluoro(oxalatoborate) was obtained as colorless solid in 55% yield.

Example 5 (Inventive)

The process was the same as described in Example 3 with the exception that 339 g triethylammonium difluoro(oxalatoborate) and a solution of 358 g 1-methyl-1-(2-((methylsulfonyl)oxy)ethyl)-pyrrolidinium methansulfonate in methanol were used resulting in a molar ratio of $K^1A$ to $KA^1$ of 1.2 1-methyl-1-(2-((methylsulfonyl)oxy)ethyl)-pyrrolidinium difluoro(oxalatoborate) was obtained as colorless solid in 60% yield.

Example 6 (Inventive)

The process was the same as described in Example 3 with the exception that 423 g triethylammonium difluoro(oxalatoborate) and a solution of 358 g 1-methyl-1-(2-((methylsulfonyl)oxy)ethyl)-pyrrolidinium methansulfonate in methanol were used resulting in a molar ratio of $K^1A$ to $KA^1$ of 1.5. 1-methyl-1-(2-((methylsulfonyl)oxy)ethyl)-pyrrolidinium difluoro(oxalatoborate) was obtained as colorless solid in 63% yield.

B Preparation Via Isopropylammonium Difluoro(Oxalatoborate)

Example 7 (Inventive)

224 g isopropylammonium difluoro(oxalatoborate) (melting point 40° C., prepared according to Example 2) was charged to a reactor, melted at 40° C. and cooled to 30° C. resulting in a supercooled melt. A solution of 345 g 1-methyl-1-(2-((methylsulfonyl)oxy)ethyl)-pyrrolidinium methansulfonate in methanol was added at once and the reaction mixture was cooled to 0° C. under stirring. The molar ratio of $K^1A$ to $KA^1$ was 1 At a temperature of 20° C. seed crystals of 1-methyl-1-(2-((methylsulfonyl)oxy)ethyl)-pyrrolidinium difluoro(oxalatoborate) were added, followed by stirring for additional 12 h. The suspension was filtered and the residue sequentially washed with portions of cold methanol. 1-methyl-1-(2-((methylsulfonyl)oxy)ethyl)-pyrrolidinium difluoro(oxalatoborate) was obtained as colorless solid in 60% yield.

Example 8 (Inventive)

The process was the same as described in Example 6 with the exception that 254 g isopropylammonium difluoro(oxalatoborate) and a solution of 326 g 1-methyl-1-(2-((methylsulfonyl)oxy)ethyl)-pyrrolidinium methansulfonate in methanol were used resulting in a molar ratio of $K^1A$ to $KA^1$ of 1.2. 1-methyl-1-(2-((methylsulfonyl)oxy)ethyl)-pyrrolidinium difluoro(oxalatoborate) was obtained as colorless solid in 65% yield.

Example 9 (Inventive)

254 g isopropylammonium difluoro(oxalatoborate) prepared according to Example 2 was charged to a reactor and melted at 65° C. A solution of 391 g 1-methyl-1-(2-((methylsulfonyl)oxy)ethyl)-pyrrolidinium methansulfonate in methanol was added at once and the reaction mixture was cooled to 0° C. under stirring. The molar ratio of $K^1A$ to $KA^1$ was 1. At a temperature of 20° C. seed crystals of 1-methyl-1-(2-((methylsulfonyl)oxy)ethyl)-pyrrolidinium difluoro(oxalatoborate) were added, followed by stirring for additional 12 h. The suspension was filtered and the residue sequentially washed with portions of cold methanol. 1-methyl-1-(2-((methylsulfonyl)oxy)ethyl)-pyrrolidinium difluoro(oxalatoborate) was obtained as colorless solid in 57% yield.

The invention claimed is:

1. A process for preparing an ammonium or phosphonium borate salt KA containing a cation K and an anion A, comprising the steps:
    (a) providing a melt of a borate salt $K^1A$; and
    (b) adding a solution of an ammonium or phosphonium salt $KA^1$ in a solvent or solvent mixture (i),
    wherein
    K is an organic ammonium or phosphonium cation;
    A is a borate anion of formula (Ia) or (Ib)

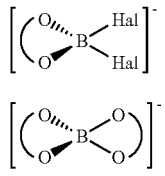

wherein Hal is halogen, and

is a bidentate radical derived from a 1,2-, 1,3- or 1,4-diol, from a 1,2-, 1,3- or 1,4-dicarboxylic acid or from a 1,2-, 1,3- or 1,4-hydroxycarboxylic acid by abstracting the two H atoms of pairs of adjacent OH groups of the respective diol, hydroxycarboxylic acid or dicarboxylic acid in 1,2-, 1,3- or 1,4-position;
    $A^1$ is an organic or inorganic anion; and
    $K^1$ is an ammonium cation different from K.

2. The process according to claim 1 wherein compound KA is precipitated during or after step (b) and is separated from the mixture containing the solvent or solvent mixture (i) and $K^1A^1$ in dissolved form.

3. The process according to claim 1, wherein during step (b) cooling is applied.

4. The process according to claim 1, wherein the temperature of the solution of the ammonium or phosphonium salt $KA^1$ added in step (b) is lower than the temperature of the melt of the borate salt $K^1A$ provided in step (a).

5. The process according to claim 1, wherein the temperature of the solution of the ammonium or phosphonium salt $KA^1$ added in step (b) is below 25° C.

6. The process according to claim 1, wherein the mixture obtained in step (b) is cooled.

7. The process according to claim 1, wherein the solvent or solvent mixture (i) contains at least one protic solvent.

8. The process according to claim 1, wherein the solvent or solvent mixture (i) contains at least one solvent selected from water and $C_1$ to $C_6$ alcohols.

9. The process according to claim 1, wherein the molar ratio of $K^1A$ to $KA^1$ used in step (b) is above 1:1.

10. The process according to claim 1, wherein A is a borate anion of formula (Ia) and Hal is F.

11. The process according to claim 1, wherein

is a bidentate radical derived from oxalic acid, salicylic acid, or phthalic acid.

12. The process according to claim 1, wherein the ammonium or phosphonium cation K is selected from $[XR^1R^2R^3R^4]^+$
    wherein X is selected from P and N;
    $R^1$, $R^2$, $R^3$, and $R^4$ are selected independently from each other from optionally substituted $C_1$-$C_{20}$ alkyl, $C_2$-$C_{20}$ alkenyl, $C_2$-$C_{20}$ alkynyl, $C_5$-$C_{12}$ (hetero)aryl, and $C_6$-$C_{30}$ (hetero)aralkyl, wherein one or more $CH_2$ groups of alkyl, alkenyl, alkynyl and (hetero)aralkyl which are not directly bound to the X-atom may be replaced by O, 1,2-epoxyethylene, cyclopropylene, $OSO_2$, $SO_2O$, $OC(O)$, $C(O)O$, $OC(O)O$, or $OC(O)C(O)O$;
    or wherein $R^1$ and $R^2$ are linked and jointly selected from a 4- to 5-membered hydrocarbon group forming together with the central X-atom a five- or six-membered heterocycle which may be substituted by one or more substituents selected from $C_1$-$C_{10}$ alkyl, and wherein one or more members of the 4- to 5-membered hydrocarbon group may be replaced by one or more O, S or NR';
    R' is selected from H, $C_1$-$C_{10}$ alkyl, $C_2$-$C_{10}$ alkenyl, $C_2$-$C_{10}$ alkynyl, $C_5$-$C_{12}$ (hetero)aryl, and $C_6$-$C_{24}$ (hetero)aralkyl, which may be substituted by one or more groups selected from F, cyclopropyl, 1,2-epoxyethyl, and sulfonate, and wherein one or more $CH_2$ groups of alkyl, alkenyl, alkynyl and (hetero)aralkyl which are not directly bound to the N-atom may be replaced by O, 1,2-epoxyethylene, cyclopropylene, $OSO_2$ or $SO_2O$.

13. The process according to claim 1, wherein cation $K^1$ is selected ammonium cations of formula $[NR^5R^6R^7R^8]^+$
    wherein $R^5$, $R^6$, $R^7$, and $R^8$ are selected independently from each other from H and $C_1$-$C_{20}$ alkyl or wherein $R^5$ and $R^6$ are linked and jointly selected from a 4- to 5-membered hydrocarbon group forming together with the central N-atom a five- or six-membered heterocycle which may substituted by one or more substituents selected from $C_1$-$C_{10}$ alkyl, and wherein one or more member of the 4- to 5-membered hydrocarbon group may be replaced by one or more O, S or NR'', and R'' is selected from H and $C_1$-$C_{10}$ alkyl.

14. The process according to claim 1, wherein $K^1$ is isopropyl ammonium.

15. The process according to claim 1, wherein anion $A^1$ is selected from $[R^9\text{—}SO_3]^-$, $Cl^-$, $Br^-$, and $I^-$, wherein $R^9$ is selected from $C_1$-$C_{20}$ alkyl, $C_2$-$C_{20}$ alkenyl, $C_2$-$C_{20}$ alkynyl, $C_5$-$C_{12}$ (hetero)aryl, and $C_6$-$C_{24}$ (hetero)aralkyl, which may be substituted by one or more groups selected from F, cyclopropyl, 1,2-epoxyethyl, and sulfonate, and wherein one or more $CH_2$ groups of alkyl, alkenyl, alkynyl and (hetero)aralkyl which are not directly bound to the $SO_3^-$ group may be replaced by O, 1,2-epoxyethylene, cyclopropylene, $OSO_2$ or $SO_2O$.

* * * * *